United States Patent [19]

Barnish et al.

[11] 4,218,474
[45] Aug. 19, 1980

[54] DERIVATIVES OF L- AND DL-4-HYDROXYPHENYLGLYCINE

[75] Inventors: Ian T. Barnish, Ramsgate; Peter E. Cross; John C. Danilewicz, both of Canterbury, England

[73] Assignee: Pfizer Inc., New York, N.Y.

[21] Appl. No.: 955,644

[22] Filed: Oct. 30, 1978

[30] Foreign Application Priority Data

Nov. 30, 1977 [GB] United Kingdom .............. 49975/77

[51] Int. Cl.$^2$ .................. C07C 103/52; C07C 103/28
[52] U.S. Cl. .............................. 424/319; 260/112.5 R; 260/559 A; 424/177; 424/324; 562/444; 562/445; 562/448
[58] Field of Search .................... 260/559 A, 112.5 R; 562/448, 444, 445; 424/177, 319, 324

[56] References Cited

U.S. PATENT DOCUMENTS

| | | | |
|---|---|---|---|
| 2,833,764 | 5/1958 | Baker et al. | 260/559 A |
| 2,868,818 | 1/1959 | Pfister et al. | 260/559 A |
| 3,725,470 | 4/1973 | Bretschneider et al. | 260/559 A |
| 4,087,520 | 5/1978 | Braun et al. | 260/112.5 R |
| 4,093,653 | 6/1978 | Boesten | 260/559 A |
| 4,111,981 | 9/1978 | Greason | 562/448 |
| 4,148,920 | 4/1979 | Barnish et al. | 424/324 |

OTHER PUBLICATIONS

Teraoa et al., J. Biochem (Japan), 70 (1971), pp. 133-142.

Flouret et al., J. Med. Chem., 1973, vol. 16, pp. 369-372.

Primary Examiner—Arthur P. Demers
Attorney, Agent, or Firm—Connolly and Hutz

[57] ABSTRACT

L- and DL-isomers of compounds of the formula

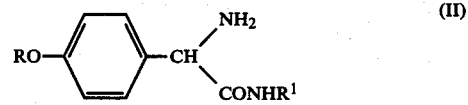

(II)

and the pharmaceutically acceptable salts thereof, wherein R is hydrogen or methyl; R$^1$ is alkynyl, alkenyl or cycloalkyl, each having from three to seven carbon atoms or alkyl having from one to six carbon atoms which may optionally be substituted by one or more groups selected from hydroxy, alkoxy, carboxy, amino, monoalkylamino, dialkylamino, phenyl and phenoxy, any such phenyl or phenoxy being optionally substituted with one or more hydroxy, alkyl or alkoxy groups, said alkyl and alkoxy optional substituents having from one to six carbon atoms; provided that R$^1$ is other than 4-hydroxy-α-carboxybenzyl or 4-methoxy-α-carboxybenzyl. Said compounds are useful in treating diseases and conditions characterized by reduced blood flow, oxygen availability or carbohydrate metabolism in the cardiovascular system. The D-isomers of the compounds of formula (II) are substantially inactive in treating such diseases and conditions.

20 Claims, No Drawings

DERIVATIVES OF L- AND DL-4-HYDROXYPHENYLGLYCINE

BACKGROUND OF THE INVENTION

1. Field of the Invention

The invention relates to novel L- and DL-isomers of compounds of formula (II) as defined herein and pharmaceutically acceptable salts thereof, their use in treating diseases and conditions of mammalian subjects including humans, which are characterized by reduced blood flow, reduced oxygen availability or reduced carbohydrate metabolism in the cardiovascular system; and pharmaceutical compositions thereof.

2. Description of the Prior Art

In Belgian Pat. No. 859,151 published on Jan. 16, 1978 (Derwent No. 08402A/05), assigned to the same assignee, known L- and DL-phenylglycines of the formula

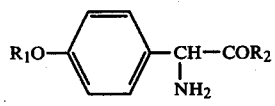

where $R_1$ is hydrogen or methyl and $R_2$ is $NH_2$, OH or completes a carboxylic ester group, are disclosed as being useful in treating diseases and conditions characterised by reduced blood flow, oxygen availability or carbohydrate metabolism in the cardiovascular system. Such conditions include ischaemic heart disease (particularly angina pectoris and myocardial infarction), cardiac failure and cerebral insufficiency. The compounds are also useful in other diseases involving defects in carbohydrate metabolism such as obesity and diabetes.

In our co-pending application, Ser. No. 900,802 filed Apr. 27, 1978, novel derivatives of L- and DL-p-hydroxyphenylglycine of the formula

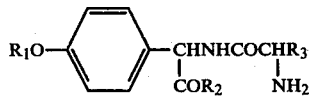

and the pharmaceutically acceptable salts thereof are disclosed as having the same utility. In the above formula (Ia) $R_1$ and $R_2$ are as defined above and $R_3$ is the residue of certain amino acids.

SUMMARY OF THE INVENTION

The present invention provides novel derivatives of L- and DL-4-hydroxyphenylglycine of the formula

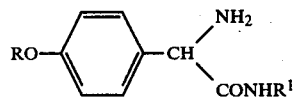

and the pharmaceutically acceptable salts thereof where R is hydrogen or methyl; $R^1$ is a member selected from the group consisting of alkynyl, alkenyl and cycloalkyl, each having from three to seven carbon atoms, alkyl having from one to six carbon atoms, $CH_2COOH$, $(CH_2)_n-NR^2R^3$, $CH_2C_6H_3R^4R^5$,

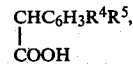

dihydroxyalkyl having from three to four carbon atoms wherein said hydroxy groups are attached to different carbon atoms, and alkyl having from two to six carbon atoms substituted by up to two unlike members selected from the group consisting of hydroxy, alkoxy having from one to six carbon atoms, carboxy, $C_6H_3R^4R^5$ and $OC_6H_3R^4R^5$ provided that when two of said members are present and are hydroxy and said alkoxy, said members are attached to different carbon atoms; n is 1 to 4, $R_2$ and $R^3$ are each hydrogen or alkyl having from one to four carbon atoms; $R^4$ and $R^5$ are each hydrogen, hydroxy, or alkyl or alkoxy each having from one to four carbon atoms; provided that $R^1$ is other than

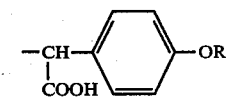

Those compounds in which $R^1$ has the above value, and which are excluded from the present invention, are included within the subject matter of our above-mentioned co-pending application, Ser. No. 900,802 filed Apr. 27, 1978.

The derivatives of L-4-hydroxyphenylglycine of formula (I) are preferred, the D-form being substantially inactive. It will therefor be appreciated that compounds of formula (II) derived from L-4-hydroxyphenylglycine will be substantially more active than the corresponding racemic, DL-compounds.

Pharmaceutically acceptable salts of compounds of the formula (II) include acid addition salts with acids containing pharmaceutically acceptable anions, e.g. the hydrochloride, hydrobromide, sulphate or bisulphate, phosphate or acid phosphate, acetate, maleate, fumarate, succinate, lactate, tartrate, citrate, gluconate, saccharate and p-toluene sulphonate salts. When $R^1$ contains a carboxy group, pharmaceutically acceptable salts also include salts formed with bases containing pharmaceutically acceptable cations, e.g. the sodium, potassium, calcium and ammonium salts.

Especially preferred compounds and salts of formula (II) are those wherein R is hydrogen. Especially preferred values for $R^1$ are alkyl having from one to four carbon atoms, $-CH_2C_6H_4OH$, alkoxyethyl or alkoxypropyl having from one to six carbons in the alkoxy group, propargyl, cyclopentyl, carboxysubstituted alkyl when derived from the naturally occuring L-α-amino acids and $CH_2CH_2NR^2R^3$ where $R^2$ and $R^3$ are each methyl, ethyl or propyl.

Particularly preferred compounds of formula (II) are:
L-N-(4-hydroxybenzyl)-2-amino-2-(4-hydroxyphenyl)acetamide,
L-N-(2-methoxyethyl)-2-amino-2-(4-hydroxyphenyl)acetamide,
L-N-isopropyl-2-amino-2-(4-hydroxyphenyl)acetamide,
L-N-propargyl-2-amino-2-(4-hydroxyphenyl)acetamide,
L-N-cyclopentyl-2-amino-2-(4-hydroxyphenyl)acetamide, and L-N-(2-diethylamino)ethyl-2-amino-2-(4-hydroxyphenyl)acetamide.

The invention further provides a method of treating mammalian subjects, including humans, suffering from a disease or condition attributable to reduced blood flow, oxygen availability or carbohydrate metabolism which comprises orally or parenterally administering to said subject a blood flow, oxygen availability or carbohydrate metabolism increasing amount of a compound of formula (II) or a pharmaceutically acceptable salt thereof.

Also provided are pharmaceutical compositions comprising a pharmaceutically acceptable carrier and a blood flow, oxygen availability or carbohydrate metabolism increasing amount of a compound of formula (II) or a pharmaceutically acceptable salt thereof.

DETAILED DESCRIPTION OF THE INVENTION

The novel compounds of formula (II) may be prepared using the classic protecting and coupling techniques of amino-acid chemistry, for example as described in "Chemistry of the Amino Acids" by J. P. Greenstein and M. Winitz, J. Wiley and Sons, Inc., New York, Vol. 2. Thus the amino group in 4-hydroxy or 4-methoxyphenylglycine is protected with a selectively removable blocking group and the carboxyl group is then reacted with an amine, of the formula $R^1NH_2$ wherein $R^1$ is as previously defined, for example using a coupling agent or an activated ester technique. In the case where the amino component itself contains a carboxyl or further free amino group this too requires protection during formation of the amide link. The protecting groups are finally removed to yield the amides of formula (II).

A convenient amino-blocking group is the t-butoxycarbonyl group. This group is readily introduced by reaction with t-butoxycarbonyl azide by the method of Grzonka et al., Synthesis, 661 (1974), and is easily removed from the final product by acid treatment. Alternative N-blocking groups such as the benzyloxycarbonyl group, which is removed by catalytic hydrogenolysis, may also be employed except in those cases where $R^1$ is alkenyl or alkynyl.

Formation of the amides may be achieved in various ways, for example in one method, the amine is reacted with a mixed anhydride, prepared from the acid by reaction with a chloroformate, e.g., iso-butylchloroformate or ethylchloroformate. Such a reaction is performed by adding the chloroformate (in slight molar excess, e.g., a 5% excess) to a solution of the N-protected-4-hydroxy (or methoxy) phenylglycine dissolved in a reaction inert organic solvent, e.g., 1,2-dimethoxyethane or tetrahydrofuran, and is advantageously performed at a low temperature, e.g., $-5°$ to $0°$ C. in the presence of a base, e.g, triethylamine.

Formation of the mixed anhydride is generally substantially complete within 10 minutes under these conditions. The amine component may then be added, preferably as a solution in an inert organic solvent, e.g., tetrahydrofuran. Formation of the amide is usually complete within several hours (e.g., 3 hours) at room temperature.

Alternatively the amine may be reacted with an activated ester derivative prepared from the acid, for example, by reaction with N-hydroxysuccinimide and dicyclohexylcarbodiimide. Thus the N-protected-4-hydroxy (or methoxy) phenylglycine may be treated in a reaction inert organic solvent (e.g. ethyl acetate or tetrahydrofuran) with a slight molar excess of N-hydroxy-succinimide and dicyclohexylcarbodiimide to effect formation of the succinimido ester. The reaction is performed at a temperature between $0°$ C. and room temperature and is ordinarily complete within several hours, typically about 3 hours. The precipitate of dicyclohexylurea may be removed by filtration, if desired, and the amine component may then be added as before; formation of the amide product generally being complete within several hours at room temperature, e.g. on standing overnight. In either case the product is isolated in a conventional manner, for example, by removal of the solvent and is further purified, if necessary, by solvent extraction as appropriate to remove unreacted starting materials or impurities, or by crystallisation.

The N-blocking group is then removed. Thus if the t-butoxycarbonyl group is employed, this may be removed by acid treatment, e.g., by dissolving the product in ethereal hydrogen chloride or with hydrogen bromide in glacial acetic acid at room temperature. Slight warming may be necessary initially, to dissolve the product, and the deprotection is then generally complete within several hours, e.g., overnight. The product is then isolated as the hydrochloride or hydrobromide salt by filtration and may be further purified as desired by conventional techniques.

When the amine reacted with the N-protected-4-hydroxy (or 4-methoxy)phenylglycine is a diamine of formula $NH_2(CH_2)_nR^2R^3$ wherein n, $R^2$ and $R^3$ are as previously defined, it is preferable to employ a large molar excess, for example, a 2 to 10 molar excess of said diamine to favor the formation of the desired monoacylated product. If necessary, the product isolated from such acylation can be purified, for example, by column chromatography on silica gel. The purification can be carried out either before or after removal of the N-protecting group, however, it is preferably done after removal of the N-protecting group.

In the case where the amine component contains a carboxyl group, i.e., when an amino acid is used in the reaction, the carboxyl group will also require protection and this is conveniently achieved by esterification typically as the methyl ester. Hydrolysis to yield the free acid is preferably performed before removal of the N-protecting group and is achieved by alkaline hydrolysis, e.g., by treatment with dilute aqueous sodium hydroxide solution at room temperature for 30 minutes.

Conversion to other pharmaceutically acceptable acid addition salts may be achieved in a conventional way e.g. by neutralization to form the free base, extraction, and reacidification of the free base with the desired acid or by ion exchange chromatography employing an anion exchange resin.

In the case where $R^1$ contains a carboxyl group, the free base or an acid addition salt may be reacted with sufficient base, for example, sodium hydroxide, potassium carbonate or calcium oxide, in the presence of water and the aqueous solution evaporated to provide the desired carboxylate salt. The latter may also be prepared by treatment of the free base or an acid addition salt with a cation exchange resin.

Starting L- and DL-4-hydroxyphenylglycines are available commercially as are the corresponding 4-methoxy compounds. Methods for resolution of the racemic compounds into the D- and L-forms are well known, see for example, U.S. Pat. No. 3,976,680. Many of the amines of formula $R^1NH_2$ employed as starting material are commercially available or may be readily obtained from available precursors by methods which are well known to those skilled in the art. Several comprehensive reviews of methods for making such amines are available, see for example, Houben-Weyl, "Methoden der Organischen Chemie", 4th edition, Volume XI/I, Georg Thieme Verlag, Stuttgart, 1957; Wagner and Zook, "Synthetic Organic Chemistry", John Wiley and Sons, Inc., New York, 1953, pp. 653-727; Sandler and Karo, "Organic Functional Group Preparation," Academic Press, New York, 1968; pp. 318-362 and "Rodd's Chemistry of Carbon Compounds" S. Coffey, Ed., Vol. 1 Part B, Elsevier Publishing Co., New York, 1965, pp. 111-121.

Alkynylamines not commercially available are prepared by methods described by Gelin, et al., *Bull. Soc. Chem. France*, 3079-3082 (1966), *Chem. Abstr.*, 66, 46058r (1967) and Dumont, et al., ibid. 588-596 (1967), *Chem. Abstr.*, 115254r (1967). The requisite amino acids of formula $R^1NH_2$ where $R^1$ is a carboxysubstituted alkyl group are commercially available or prepared by methods set forth in the above reviews and in Greenstein and Winitz, "Chemistry of the Amino Acids," Vol. 3, J. Wiley and Sons, Inc., New York, 1961.

The requisite diamines of formula $R^1NH_2$, if not commercially available, are prepared by well known method, e.g., by reduction of the corresponding nitriles or amide with lithium aluminum hydride. Many of the amino glycols and their alkyl ethers are known. Those that are not are prepared by well known techniques such as by hydrolysis or alcoholysis of the appropriate epoxynitrile, epoxyaldehyde or epoxyketone to obtain an intermediate glycol or monoether thereof, followed by reduction of the intermediate nitrile or oxime.

The compounds of the formula (II) may be administered to patients in admixture with or dissolved in a pharmaceutically acceptable carrier selected with regard to the intended route of administration and standard pharmaceutical practice. For example, they may be administered orally in the form of tablets or capsules containing a unit dose of the compound of the formula (II) together with such excipients as corn starch, calcium carbonate, dicalcium phosphate (CaHPO4), alginic acid, lactose, magnesium stearate, talc, or certain complex silicates. The tablets are typically prepared by granulating the ingredients together and compressing the resulting mixture to tablets of the desired size. The capsules are typically prepared by granulating the ingredients together and filling them into hard gelatin capsules of the appropriate size to contain the ingredients.

The compounds of the invention may also be administered parenterally, for example by intramuscular, intravenous or subcutaneous injection. For parenteral administration, they are best used in the form of a sterile aqueous solution which may contain other solutes, for example enough salts (e.g. sodium acetate, sodium lactate, sodium succinate or sodium chloride) or dextrose to make the solution isotonic. A pharmaceutically acceptable organic solvent such as polyethylene glycol or ethanol may also replace part of the water. An antioxidant such as sodium metabisulphite may also be present, typically in an amount up to 0.1% by weight. Such parenteral formulations may be prepared by conventional methods. For example, in a typical procedure involving the preparation of a succinate-containing intravenous formulation, a 0.2 molar solution of succinic acid may be mixed with a 0.2 molar solution of sodium hydroxide to give a solution of pH 5. The compound of the formula (II) is then typically dissolved in the succinate solution in an amount of 1-2% on a weight/volume basis. The resulting solution may then be sterilized, for example by filtration, through a bacteria-proof filter under aseptic conditions into sterile containers.

Alternatively, stable parenteral formulations based on isotonic saline solution may be prepared by successively dissolving an antioxidant, e.g. sodium metabisulphite, and sodium chloride in nitrogen-sparged water to give an approximately 0.1 molar sodium chloride solution, dissolving the compound of formula (II) in solution in an amount of 1-2% on a weight/volume basis and adjusting the pH to about 4 with 0.1 N hydrochloric acid. The solution is then sterilized and filled into containers as already described. Suitable containers are, for example, sterile glass vials of an appropriate size to contain the desired volume of solution, which volume will typically contain one or more unit doses of the compound of the formula (II). The compounds of the formula (II) may also be administered by the infusion of a parenteral formulation as described above into a vein.

For oral administration to human patients, the daily dosage level of L-form of a compound of the formula (II) will be from 1 to 50, preferably 2-20 mg./kg. per day for a typical adult patient (70 kg.). For parenteral administration the daily dosage level of the L- form of a compound of the formula (II) will be from 1-10, preferably 2-5 mg./kg. per day, for a typical adult patient. Thus tablets or capsules would contain from 20 mg. to 1 g. of the active compound for administration orally up to 4 times a day. Dosage units for parenteral administration would contain from 70-700 mg. of the active compound. The dosage level of the racemic (DL) form of the compounds will of course be approximately twice that of the L-form.

It should of course be appreciated that in any event the physician will determine the actual dosage which will be most suitable for the individual and it will vary with the age, weight and response of the patient. The above dosages are exemplary of the average patient, there may of course be individual cases where higher or lower dosage ranges are merited.

The utility of the compounds of the formula (II) for treating disease or conditions characterized by reduced blood flow, oxygen availability or carbohydrate metabolism in the cardiovascular system, or other disease or condition involving a defect in carbohydrate metabolism, particularly diabetes and obesity, is assessed by the their ability:

(1) to increase the oxidation of glucose and/or pyruvate by isolated rat muscle preparations in vitro;
(2) to increase the proportion of the active form of the enzyme pyruvate dehydrogenase (PDH) in organs of animals in vivo;
(3) to reduce oxygen demand and affect the relative utilization of carbohydrate and lipid metabolites by the electrically-paced heart of anesthetized dogs in the presence or absence of an isoprenaline stimulus; and
(4) to decrease the blood glucose levels in animals made diabetic by chemical lesion of the pancreas.

Activity in tests for (1) demonstrates the utility of the compounds in the treatment of ischaemic heart disease, cardiac failure, cerebral insufficiency, maturity-onset diabetes or obesity. Activity in tests for (2) further demonstrates their utility in the treatment of these diseases or conditions and, in particular, activity in an animal heart in vivo demonstrates utility in the treatment of ischaemic heart disease and cardiac failure, while activity in animal brain in vivo is a measure of utility in the treatment of cerebral insufficiency. Activity in tests for (3) further demonstrates their utility in the treatment of ischaemic heart disease and cardiac failure. Activity in test for (4) is a further measure of their utility in the treatment of diabetes.

Representative compounds of the formula (II) have been tested for their ability to increase the oxidation of glucose and/or pyruvate as follows:

Diaphragm tissue is obtained from rats fed on a high fat diet similar to 'Diet B' described by Zaragoza and Felber [*Horm. Metab. Res.*, 2, 323 (1970)]. Pyruvate oxidation by such tissue is assessed by measurement of the rate of incorporation of carbon-14 from carbon-14-labelled pyruvate into carbon dioxide in vitro, as described by Bringolf [*Eur. J. Biochem.*, 26, 360 (1972)]. The rate of pyruvate oxidation is depressed by 50%–75% compared with that by diaphragm tissue from rats fed on a normal diet. When the L- and DL-compounds of the formula (II) are added to the medium, they are found to stimulate pyruvate oxidation by diaphragm tissue from fat-fed rats in a dose dependent manner.

The degree of stimulation at a concentration of 0.5 mmoles for the compounds provided in certain Examples is shown in the following Table:

| Compound of Example | % Stimulation | Compound of Example | % Stimulation |
|---|---|---|---|
| 1 | 72 | 13 | 45 |
| 2 | 108 | 14 | 76 |
| 3 | 15 | 15 | 55 |
| 4 | 82 | 16 | 67 |
| 5 | 23 | 17 | 41 |
| 6 | 38 | | |

The degree of stimulation by the corresponding racemic (DL) compounds is found to be somewhat lower than the above values. The D-isomers of the corresponding compounds do not stimulate pyruvate oxidation to an appreciable extent.

The ability of compounds of formula (II) to increase the proportion of the active form of the pyruvate dehydrogenase enzyme has been measured in the following test:

Rats fed on a high fat diet as in the previous test, are treated either with placebo or with the compound of formula (II) by subcutaneous or intravenous injection or by oral administration. After 1½ hours the rat hearts are removed and homogenized under conditions which minimize changes in the proportion of the pyruvate dehydrogenase enzyme (PDHt) which is present in the active form, as described by Whitehouse and Randle [*Biochem. J.*, 134, 651 (1973)]. The total amount of the enzyme present (PDHt) and the amount which is present in the active form (PDHa) are assessed by a method similar to that described by Taylor et al. [*J. Biol. Chem.*, 248, 73 (1973)]. The fat-feeding process is found to depress the ratio PDHa/PDHt from a normal value of about 0.7 to a value in the range from 0.05 to 0.2. Treatment of fat-fed rats with L- and DL-compounds of formula (II) either parenterally or orally, increases this ratio in a dose-dependent manner.

The increase in the PDHa/PDHt ratio affected by the L-compounds of formula (II) at a dosage level of 0.6 mg./kg. via the oral or sub-cutaneous route is shown in the following Table:

| Compound of Example | PDHa/PDHt ratio placebo | PDHa/PDHt ratio Compound | Compound of Example | PDHa/PDHt ratio placebo | PDHa/PDHt ratio Compound |
|---|---|---|---|---|---|
| 1 | 0.14 | 1.00 | 13 | 0.14 | 0.55 |
| 2 | 0.13 | 0.65 | 14 | 0.14 | 0.88 |
| 3 | 0.14 | 0.56 | 15 | 0.18 | 0.25 |
| 4 | 0.18 | 0.73 | 16 | 0.12 | 0.31 |
| 5 | 0.18 | 0.88 | 17 | 0.18 | 0.31 |
| 6 | 0.21 | 0.78 | | | |

When the above test is repeated with the corresponding DL-compounds, the ratios obtained are somewhat lower. When the corresponding D-isomers are employed the ratios do not differ significantly from the placebo values.

The preparation of the novel compounds of the invention is illustrated by the following Examples:

EXAMPLE 1

A.

(L)-N-tert-Butoxycarbonyl-2-(4-hydroxyphenyl)glycine

This was obtained from L(+)-2-(4-hydroxyphenyl)glycine and t-butyloxycarbonylazide by the method of Grzonka and Lammek (Synthesis, 1974, 661). Crystallisation from hexane-ethyl acetate afforded material suitable for further synthesis in yields typically 69–90%, M.P. 114°–115° C. (decomp.); $[\alpha]_D^{28} + 128°$ (1.02%, methanol). Recrystallisation from aqueous ethanol afforded pure material of M.P.=115°–117° C. (decomp.); $[\alpha]_D^{28} + 135°$ (1.01%, methanol).

B.

(L)-N-(4-Hydroxybenzyl)-2-(tert-butoxycarbonylamino)-2-(4-hydroxyphenyl)acetamide The product from Part A, above, (5.3 g., 0.02 mole) was dissolved in dry tetrahydrofuran (50 ml.) and the solution was stirred and cooled to 0° C. Triethylamine (2.1 g., 0.021 mole) was added followed by isobutyl chloroformate (2.77 g., 0.0203 mole), and the mixture was stirred and allowed to stand at −5° C. to 0° C. for a few minutes. A solution of 4-hydroxybenzylamine (2.82 g., 0.02 mole) in dry tetrahydrofuran (10 ml.) was then added dropwise over a period of 10 minutes to the stirred solution which was allowed to warm to room temperature and stirred for a further three hours. The suspension was evaporated to dryness and the residual solid was partitioned between water and ethyl acetate. The aqueous layer was separated and extracted with ethyl acetate. The combined organic extracts were dried over sodium sulphate, filtered, and the solvent evaporated to yield an oil which solidified on trituration with petroleum ether (b.p. 60°–80° C.) to give the amide (3.9 g., 50%), M.P. 60° C. $[\alpha]_D^{25} + 50.7°$ (1% in methanol).

C.

(L)-N-(4-Hydroxybenzyl)-2-amino-2-(4-Hydroxyphenyl)acetamide hydrochloride

The crude product from Part B (3 g.) was dissolved in ethyl acetate (10 ml.) and to this was added ethereal HCl (20 ml.) with stirring. A gum was rapidly formed which solidified on continued stirring to give a brown solid. Stirring was continued overnight, the solid was collected by filtration, washed with dry ether and recrystallised from a mixture of isopropyl alcohol and diethyl ether to yield the hydrochloride salt (1.3 g., 42%), M.P. 185°–190° C., $[\alpha]_D^{25} +50.7°$ (1% in methanol).

Found: C, 58.5; H, 5.8; N, 8.8. $C_{15}H_{16}N_2O_3 \cdot HCl$ requires C, 58.35; H, 5.55, N, 9.05%.

EXAMPLES 2 TO 6

The following compounds were prepared by the general method of Example 1 using L-N-tert-butoxycarbonyl-2-(4-hydroxyphenyl)glycine and the appropriate amine. Table I shows the compounds prepared together with their melting points, optical rotation and analytical data.

| R | $R^1$ |
|---|---|
| H | $C_6H_5CH_2$ |
| H | $2\text{-HOC}_6H_4CH(CH_3)$ |
| H | $4\text{-CH}_3OC_6H_4CH_2CH_2$ |
| H | $2,3\text{-}(CH_3O)_2C_6H_3CH_2$ |
| H | $4\text{-i-}C_4H_9OC_6H_4CH_2CH_2CH_2$ |
| H | $3,5\text{-}(CH_3)_2C_6H_3CH_2$ |
| H | $3,4\text{-}(HO)_2C_6H_3CH_2$ |
| $CH_3$ | $CH_3(CH_2)_4CH(C_6H_5)$ |
| $CH_3$ | $C_6H_5CH_2CH_2CH_2CH_2$ |
| $CH_3$ | $CH_3CH_2$ |
| $CH_3$ | $n\text{-}C_6H_{13}$ |

TABLE I

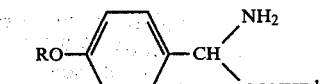

(L)

| Example No. | $R^1$ | Salt Form | m.p. °C. | $[\alpha]_D^{25}$ | Analysis % (Theoretical in brackets) | | |
|---|---|---|---|---|---|---|---|
| 2 | $-CH(CH_3)_2$ | HBr | 218° (dec.) | +67.5° (1% MeOH) | C, 45.85 (C, 45.7 | H, 5.85 H, 5.9 | N, 9.8 N, 9.7) |
| 3 | $-C(CH_3)_3$ | HCl | 168° | +97.6° (1% MeOH) | C, 54.9 (C, 54.75 Calculated for | H, 7.4 H, 7.5 ¼ H_2O) | N, 9.95 N, 10.6) |
| 4 | $-CH_2C\equiv CH$ | HCl | — | +66.6° (0.5% MeOH) | C, 53.4 (C, 53.55 (Calculated for | H, 5.5 H, 5.6 ⅜ H_2O) | N, 11.15 N, 11.35) |
| 5 | cyclopentyl | HCl | 148° (dec.) | +55.3° (1% MeOH) | C, 56.8 (C, 56.7 (Calculated for | H, 6.95 H, 7.15 ¼ H_2O) | N, 9.8 N, 10.2) |
| 6 | $-CH_2CH_2N(CH_2CH_3)_2$ | 2HCl | 80° (dec.) | +70° (1% MeOH) | C, 49.8 (C, 50.05 (Calculated for H_2O, | H, 8.6 H, 8.05 ⅜ C_3H_7OH) | N, 11.3 N, 10.95) |

EXAMPLE 7

(L)-N-(4-Hydroxybenzyl)-2-amino-2-(4-methoxyphenyl)acetamide.HCl

By employing L(+)-2-(4-melthoxyphenyl)glycine in the procedure of Example 1, Part A, and carrying the resulting (L)-N-t-butoxycarbonyl-2-(4-methoxyphenyl)glycine through the procedures of Example I, Parts B and C, the title compound is similarly obtained.

EXAMPLE 8

When the procedures of Examples 1 through 7 are repeated, but employing racemic 2-(4-hydroxyphenyl)glycine or 2-(4-methoxyphenyl)glycine in place of the corresponding L-isomers as starting material in each case, the corresponding DL-(racemic)compounds are obtained.

EXAMPLE 9

When the procedures of Examples 1 through 8 are repeated, but employing the appropriate amine of formula $R^1NH_2$ in each case, the following compounds are provided as their hydrochloride salts.

| | |
|---|---|
| $CH_3$ | $(CH_3CH_2)_2CH$ |
| $CH_3$ | cyclohexyl |
| $CH_3$ | cyclopentyl |
| H | cycloheptyl |
| H | cyclohexyl |
| H | cyclopropyl |
| H | $CH_2CH=CHCH_2$ |
| H | $CH_2=CCH_2$ |
| H | $CH_3(CH_2)_3CH=CHCH_2$ |
| H | $HC\equiv CCH_2CH_2$ |
| H | $HC\equiv C(CH_2)_3CH_2$ |
| $CH_3$ | $HC\equiv C(CH_2)_4CH_2$ |
| $CH_3$ | $CH_3C\equiv CCH_2$ |
| $CH_3$ | $CH_3OCH_2CH(CH_3)$ |
| $CH_3$ | $n\text{-}C_4H_9OCH_2CH_2CH_2$ |
| H | $CH_3CH_2OCH_2(CH_2)_3CH_2-$ |
| H | $HOCH_2CH(nC_4H_9)$ |
| H | $CH_3CH_2CH_2OCH_2CH_2CH_2$ |
| H | $iso\text{-}C_5H_{11}OCH_2CH_2CH_2$ |
| H | $n\text{-}C_6H_{13}OCH_2CH(CH_3)CH_2$ |
| H | $CH_3OCH_2CH(OH)CH_2-CH_2$ |
| H | $(CH_3)_2NCH_2CH_2$ |
| $CH_3$ | $(CH_3CH_2)_2NCH_2(CH_2)_4CH_2$ |
| $CH_3$ | $C_6H_5OCH_2CH_2$ |
| $CH_3$ | $C_6H_5OCH_2(CH_2)_4CH_2$ |
| $CH_3$ | $4\text{-HOC}_6H_4OCH_2CH_2CH_2$ |
| $CH_3$ | $2\text{-CH}_3OC_6H_4OCH_2CH_2$ |
| H | $2,4\text{-}(CH_3O)_2C_6H_3OCH_2CH_2$ |
| H | $2,4\text{-}(tert\text{-}C_4H_9C_6H_3OCH_2CH(OH)CH_2$ |
| H | $2,4\text{-}(CH_3)_2C_6H_3OCH_2CH_2CH_2$ |
| H | $(n\text{-}C_3H_7)_2NCH_2CH_2$ |

EXAMPLE 10

(L)-N-(2-hydroxyethyl)-2-amino-2-(4-hydroxyphenyl)-acetamide hydrochloride

By employing ethanolamine instead of 4-hydroxybenzylamine in the procedure of Example 1, Part B and hydrolysing the product by the procedure of Example 1, Part C, the title compound is similarly obtained.

EXAMPLE 11

(L)-N-(2-aminoethyl)-2-amino-(4-hydroxyphenyl)-acetamide Dihydrochloride (L)-N-tert-Butoxycarbonyl-2-(4-hydroxyphenyl)glycine, 0.02 mole is converted to the corresponding mixed anhydride employing ethyl chloroformate in place of isobutyl chloroformate in the procedure of Example 1, Part B. The resulting solution in dry tetrahydrofuran is then added dropwise under anhydrous conditions to a stirred solution of ethylenediamine (12 g, 0.2 mole) in 200 ml of tetrahydrofuran while maintaining the mixture at 0° C. The mixture is stirred for an additional 30 minutes then allowed to warm to room temperature and stirred for four hours. The solvent is evaporated and the residue partitioned between water and ethyl acetate. The organic layer is separated, washed with dilute aqueous sodium bicarbonate, water, dried ($MgSO_4$), and evaporated to dryness to provide the 2-tert-butoxycarbonyl derivative of the desired compound. This is hydrolyzed by the procedure of Example 1, Part C to provide the title compound.

If desired, the product is purified by dissolving it in water, neutralising and extracting with ether. The ether extracts are evaporated to a small volume and the residue subjected to column chromatography on silica gel. The fractions containing the desired product are evaporated to dryness to obtain the free base. Alternatively, the free base is taken up in ether, an equivalent amount of anhydrous hydrogen chloride added, the precipitated hydrochloride salt collected by filtration and dried.

EXAMPLE 12

Employing the procedures of Examples 10 and 11 but using the appropriate amine of formula $R^1NH_2$ in place of the ethanolamine and ethylenediamine used in those examples, the following derivatives of 4-hydroxyphenylglycine and 4-methoxyphenylglycine are obtained as the hydrochloride salts.

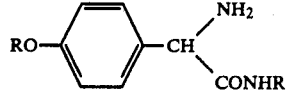

| R | $R^1$ |
|---|---|
| $CH_3$ | $HOCH_2CH_2$ |
| $CH_3$ | $NH_2CH_2CH_2$ |
| $CH_3$ | $HOCH_2CH(CH_3)$ |
| $CH_3$ | $HOCH_2CH_2CH_2$ |
| H | $(HOCH_2)_2CH$ |
| H | $HOCH_2(CH_2)_3CH_2$ |
| H | $HOCH_2CH(n-C_4H_9)$ |
| H | $HOCH_2CH(CH_2CH_3)$ |
| $CH_3$ | $HOCH_2C(CH_3)_2$ |
| $CH_3$ | $(HOCH_2)_2C(CH_3)$ |
| $CH_3$ | $HOCH_2(CH_2)_4CH_2$ |
| $CH_3$ | $(CH_3)_2NCH_2CH_2$ |
| H | $(n-C_4H_9)_2NCH_2CH_2CH_2$ |
| H | $tert-C_4H_9NHCH_2CH_2$ |
| H | $CH_3NHCH_2CH_2$ |
| H | $tert-C_4H_9NHCH_2CH_2CH_2$ |
| $CH_3$ | $CH_3CH(NH_2)CH_2$ |
| $CH_3$ | $CH_3CH(CH_2NH_2)$ |
| $CH_3$ | $NH_2CH_2(CH_2)_4CH_2$ |
| $CH_3$ | $HOCH_2CH(n-C_4H_9)$ |

EXAMPLE 13

A.

(L)-N-methyl-2-(tertiary-butyloxycarbonylamino)-2-(4-hydroxyphenyl)acetamide

A solution of dicyclohexylcarbodiimide (5.1 g., 0.0248 mole) in ethyl acetate (50 ml.) was added to a stirred solution of (L)-N-tert-butoxycarbonyl-2-(4-hydroxyphenyl)glycine (6.0 g., 0.0225 mole) and N-hydroxy succinimide (2.7 g., 0.0235 mole) in ethyl acetate (75 ml.). The mixture was stirred at room temperature for 2.5 hours and then cooled to 0° C. and the precipitate of dicyclohexylurea was removed by filtration. Methylamine (2.4 g. as a 33% solution by weight in ethanol) was added to the filtrate and the stirring was continued overnight. Water (50 ml.) was added and the mixture shaken and filtered to remove a small amount of insoluble material. The organic layer was separated, washed, dried over sodium sulphate, filtered and evaporated to give an oil. Trituration with warm hexane gave the crude amide as a solid (4.23 g., 70%; M.P. 165°–167° C., $[\alpha]_D^{25} + 125.1°$ (1% in methanol).

B.

(L)-N-methyl-2-Amino-2-(4-hydroxyphenyl)acetamide hydrochloride

The crude mixture from Part A, above, (2.8 g.) was dissolved in warm ethyl acetate (20 ml.), cooled and ethereal HCl (30 ml.) added. The mixture was stirred overnight at room temperature and the resulting precipitate was collected by filtration and dried to yield the hydrochloride salt (2.1 g., 75%), M.P. 236°–239° C., $[\alpha]_D^{25} + 128.2°$ (1% methanol). Found: C, 49.9; H, 6.1; N, 12.5. $C_9H_{12}N_2O_2 \cdot HCl$ requires C, 49.9; H, 6.05; N, 12.9%.

EXAMPLES 14 TO 15

The following compounds were prepared by the general method of Example 13 using (L)-N-tert-butyloxycarbonyl-2-(4-hydroxyphenyl)glycine and the appropriate amine. Table II shows the compounds prepared together with their melting points, optical rotation and analytical data.

TABLE II $$HO-\phenyl-CH(NH_2)(CONHR^1) \quad (L)$$

| Example No. | R¹ | Salt Form | m.p. °C. | $[\alpha]_D^{25}$ | Analysis % (Theoretical in brackets) |
|---|---|---|---|---|---|
| 14 | —CH₂CH₂OCH₃ | HCl | 135° (with softening) | +73.0 (1% MeOH) | C, 49.8  H, 6.6  N, 10.2 (C, 49.8  H, 6.65  N, 10.55) (Calculated for ¼ H₂O) |
| 15 | —CH₂CH(OH)CH₂O—(phenyl with CH₃O) (DL) | HCl | 105° (dec.) | +74.5 (1% MeOH) | C, 59.1  H, 6.2  N, 7.55 (C, 58.9  H, 6.3  N, 7.65) |

EXAMPLE 16

A. N-[(L)-N-tert-Butyloxycarbonyl-2-(4-hydroxyphenyl)-glycyl]-L-tyrosine

(L)-N-tert-Butyloxycarbonyl-2-(4-hydroxyphenyl)glycine (5.23 g., 0.02 mole) was dissolved in tetrahydrofuran (50 ml.) and the solution was stirred and cooled to −5° C. Triethylamine (2.9 ml., 0.0209 mole) was added followed by the dropwise addition of ethylchloroformate (2.2 g., 0.213 mole) over a period of ten minutes. A solution of L-tyrosine methyl ester (3.9 g., 0.020 mole) in tetrahydrofuran (25 ml.) was then added over fifteen minutes and the solution was allowed to warm to room temperature and stirred for a further three hours. The suspension was evaporated to dryness and the residual solid was partitioned between water and ethyl acetate. After filtration the organic layer was separated and washed in turn with water, 2 N hydrochloric acid, water, dilute sodium bicarbonate and water. The solution was dried over sodium sulphate and the solvent evaporated to yield a viscous oil. The product was taken up in dioxan (150 ml.) and water (35 ml.) was added. The solution was stirred at room temperature while a solution of sodium hydroxide (2.2 g. in 50 ml. water) was slowly added. Stirring was continued for a further one half hour and water (35 ml.) was then added and the pH adjusted to 3–7 with aqueous citric acid. The product was extracted into ethyl acetate, the extract dried and evaporated to give a glass which was triturated with hexane to give the N-protected dipeptide as a crystalline solid (4.0 g., 45%).

B. N-[(L)-2-(4-Hydroxyphenyl)glycyl]-(L)-tyrosine hydrochloride

The product from Part A, above, was dissolved in ethyl acetate (10 ml.) and saturated ethereal HCl (15 ml.) was added. The mixture was stirred at room temperature for one half hour and then evaporated to dryness. The residue was triturated with warm ethyl acetate (10 ml.) and dried to yield the hydrochloride salt (1.75 g. 50%), M.P. 231°–234°, (decompositon), $[\alpha]_D^{25}$ +15.1° (1% methanol). Found: C, 55.4; H, 5.2; N, 7.85. $C_{17}H_{18}N_2O_5 \cdot HCl$ requires C, 55.65; H, 5.2; N, 7.65%.

EXAMPLE 17

Glycine methyl ester was reacted with L-N-tert-butyloxycarbonyl-2-(4-hydroxyphenyl)glycine by the general method of Example 16, Part A. The product was dissolved in dioxan and treated with ethereal hydrogenchloride as described in Example 16, Part B, to yield N-[(L)-2-(4-hydroxyphenyl)glycyl]-glycine hydrochloride dioxanate, M.P. 142°–147° C., $[\alpha]_D^{25}$ +9.8° (1% methanol). Found C, 47.3; H, 5.8; N, 8.0. $C_{10}N_{12}N_2O_4 \cdot HCl \cdot C_4H_8O_2$ requires: C, 48.2; H, 6.1; N, 8.0%.

EXAMPLE 18

By employing the methyl or ethyl ester of the appropriate amino acid in place of L-tyrosine methyl ester and optionally (L)-N-tert-butoxycarbonyl-2-4-(methoxyphenyl)glycine in place of the corresponding 4-hydroxyphenylglycine derivative in the procedure of Example 16, in each case the following compounds are obtained in like manner as the hydrochloride salts.

$$RO-\phenyl-CH(NH_2)(CONHR^1)$$

| R | R¹ |
|---|---|
| H | CH₂CH₂COOH |
| H | (L)-CHCH(CH₃)₂  \| COOH |
| H | (DL)-CHCH₂CH(CH₃)₂  \| COOH |
| CH₃ | (L)-CHCH(CH₃)CH₂CH₃  \| COOH |
| CH₃ | (DL)-CH—(CH₂)₄CH₃  \| COOH |
| CH₃ | (L)-CHCH₂C₆H₅  \| COOH |
| H | (DL)-CHCH₂OH  \| COOH |
| H | (DL)-CHCH₂CH₃  \| COOH |
| H | (DL)-CH—(CH₂)₂CH₂COOH  \| COOH |

EXAMPLE 19

(L)-N-(4-Hydroxybenzyl)-2-amino-2-(4-hydroxyphenyl)acetamide Free Base

The hydrochloride salt obtained in Example 1, Part C (1.0 g.) dissolved in water, is neutralized by addition of 2 N potassium hydroxide or 2 N sodium hydroxide and extracted with ethyl ether. The combined extracts are dried (MgSO$_4$) and evaporated to dryness in vacuo to provide the free base.

The hydrochloride salts provided in Examples 2 through 15 are converted to the corresponding free bases in a similar manner.

EXAMPLE 20

Isoelectric Precipitation of Dipeptides

The preparation of dipeptides of formula II wherein R$^1$ is a carboxyl-containing moiety is illustrated as follows:

N-[(L)-2-(4-Hydroxyphenyl)glycyl]-(L)-tyrosine hydrochloride, obtained as described in Example 16, is dissolved in a minimum amount of water. To the solution is added dropwise dilute sodium hydroxide solution until the isoelectric point is reached (pH 5-6) as evidenced by heavy precipitation. The resulting mixture is allowed to stand at 0°-5° C. over night and the precipitated dipeptide collected by filtration and dried.

The remaining dipeptides of formula (II) are obtained in like manner.

EXAMPLE 21

Carboxylate Salt Formation

A dipeptide provided by the procedure of Example 20 is reslurried in a small amount of water and one equivalent of sodium hydroxide is added. The resulting solution is stirred for 5-10 minutes and evaporated to dryness in vacuo to obtain the desired sodium salt.

When the above procedure is repeated but employing other alkaline reagents in place of sodium hydroxide such as, for example, potassium carbonate, ammonium hydroxide, the corresponding potassium, ammonium, calcium and magnesium salts are similarly obtained.

EXAMPLE 22

Acid Addition Salts

A free base provided by the procedure of Example 19, a dipeptide provided as described in Example 20 or a carboxylate salt provided by the procedure of Example 21 is reslurried in a small amount of water and an equivalent amount of acid (two or three equivalents for a carboxylate salt) such as hydrochloric, hydrobromic, sulfuric, phosphoric, acetic, maleic, fumaric, tartaric, citric, gluconic, saccharic or p-toluenesulfonic acid is added. The resulting mixture is stirred for about 15 minutes then evaporated to dryness or precipitated by addition of a cosolvent such as, for example, methanol, ethanol or acetone.

EXAMPLE 23

Parenteral Solutions

A. Glacial acetic acid (12.0 gm.,) and sodium acetate anhydrous (16.4 gm) are each dissolved in 1000 ml. of freshly distilled water to produce 0.2 molar solutions. 148.0 ml. of the acetic acid solution is then mixed with 352.0 ml. of the sodium acetate solution and the mixture made up to 1000 ml. with freshly distilled water. (L)-N-(4-Hydroxybenzyl)-2-amino-2-(4-hydroxyphenyl)acetamide hydrochloride, 10 g., is then added and the resulting 1% w/v solution is then sterilized by filtration through a suitable bacteria-proof filter under aseptic conditions into sterile 50 ml. glass vials, which when filled with 30 ml. of the final solution, contain 300 mg. of the active ingredient.

B. Succinic acid (23.62 gm.) and sodium hydroxide 98 g.) are each dissolved in 100 ml. of freshly distilled water to produce 0.2 molar solutions. 250 ml. of the succinic acid solution is then mixed with 267.0 ml. of the sodium hydroxide and the mixture made up to 1000 ml. with freshly distilled water. (L)-N-(2-Methoxyethyl)-2-amino-2-(4-hydroxyphenyl)acetamide is then added and the resulting 1% w/v solution is then sterilized as in Part A, above. Sterile 50 ml. glass vials, when filled with 40 ml. of the final solution, contain 400 mg. of the active ingredient.

EXAMPLE 24

The following are typical tablet or capsule formulations containing (L)-N-(4-hydroxybenzyl)-2-amino-2-(4-hydroxyphenyl)acetamide hydrochloride as active ingredient:

|  | mg./tablet or capsule | | | | |
|---|---|---|---|---|---|
|  | A | B | C | D | E |
| active ingredient | 500 | 100 | 100 | 25 | 25 |
| lactose | 30 | 170 | — | 220 | — |
| corn starch | 60 | 80 | — | 105 | — |
| microcrystalline cellulose ("Avicel")* | — | — | 170 | — | 220 |
| glycine | — | — | 80 | — | 105 |
| Fine silica ("Aerosil")* | — | 0.35 | 0.35 | 0.35 | 0.35 |
| Magnesium stearate* | 5 | 3 | 3 | 3 | 3 |
|  | 595 |  | 353.35 |  |  |

*9:1 blend with sodium lauryl sulphate. "Avicel" and "Aerosil" are Trademarks.

For formulations A, B, and D, the ingredients are thoroughly blended together, and then either filled directly into hard gelatin capsules of appropriate size, or granulated and compressed into tablets of the desired size. For formulations C and E, the ingredients are thoroughly blended together and slugged. The slugs are broken down into granules, and then either filled into capsules of the appropriate size, or directly compressed into tablets of the desired size.

In formulations A, B and D, the lactose may be replaced by equal amounts of calcium carbonate or dicalcium phosphate (CaHPO$_4$).

EXAMPLE 25

Example 24 is repeated using the same amount of racemic (DL)-N-(4-hydroxybenzyl)-2-amino-2-(4-hydroxyphenyl)acetamide hydrochloride as that of the L-isomer. Of course, twice as many capsules or tablets of this example may be required to be taken for a single therapeutic administration as are required of the tablets or capsules of Example 24.

What is claimed is:

1. L- and DL-isomers of a compound of the formula

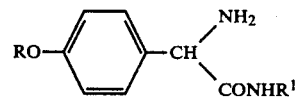

and the pharmaceutically acceptable salts thereof, wherein R is hydrogen or methyl;

R$^1$ is a member selected from the group consisting of alkynyl, alkenyl, cycloalkyl, each having from three to seven carbon atoms, alkyl having from one to six carbon atoms, CH$_2$COOH, (CH$_2$)$_n$NR$^2$R$^3$, CH$_2$C$_6$H$_3$R$^4$R$^5$,

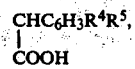

dihydroxyalkyl having from three to four carbon atoms wherein said hydroxy groups are attached to different carbon atoms, and alkyl having from two to six carbon atoms substituted by up to two unlike members selected from the group consisting of hydroxy, alkoxy having from one to six carbon atoms, carboxy, $C_6H_3R^4R^5$ and $OC_6H_3R^4R^5$ provided that when two of said members are present and are hydroxy and said alkoxy, said members are attached to different carbon atoms; n is 1 to 4, $R^2$ and $R^3$ are each hydrogen or alkyl having from one to four carbon atoms; $R^4$ and $R^5$ are each hydrogen, hydroxy, alkyl or alkoxy having from one to four carbon atoms; further provided that $R^1$ is other than

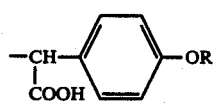

2. The L-isomer of the compounds according to claim 1.

3. A compound according to claim 2 wherein R is hydrogen.

4. A compound according to claim 3 wherein $R^1$ is a member selected from the group consisting of 4-hydroxybenzyl, 2-methoxyethyl, isopropyl, propargyl, cyclopentyl and 2-diethylaminoethyl.

5. The compound according to claim 1: L-N-(4-hydroxybenzyl)-2-amino-2-(4-hydroxyphenyl)acetamide.

6. The compound according to claim 1: L-N-(2-methoxyethyl)-2-amino-2-(4-hydroxyphenyl)acetamide.

7. The compound according to claim 1: L-N-isopropyl-2-amino-2-(4-hydroxyphenyl)acetamide.

8. The compound according to claim 1: L-N-propargyl-2-amino-2-(4-hydroxyphenyl)acetamide.

9. The compound according to claim 1: L-N-cyclopentyl-2-amino-2-(4-hydroxyphenyl)acetamide.

10. The compound according to claim 1: L-N-(2-diethylamino)ethyl-2-amino-2-(4-hydroxyphenyl)acetamide.

11. A method of treating a mammaliam subject suffering from a disease or condition attributable to reduced blood flow or oxygen availability which comprises orally or parenterally administering to said subject a blood flow or oxygen availability increasing amount of an L- or DL-isomer of a compound of the formula

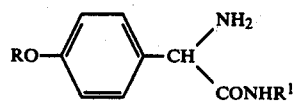

and the pharmaceutically acceptable salts thereof, wherein R is hydrogen or methyl;

$R^1$ is a member selected from the group consisting of alkynyl, alkenyl, cycloalkyl, each having from three to seven carbon atoms, $CH_2COOH$, $(CH_2)_nNR^2R^3$, $CH_2C_6H_3R^4R^5$,

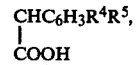

dihydroxyalkyl having from three to four carbon atoms wherein said hydroxy groups are attached to different carbon atoms, and alkyl having from two to six carbon atoms substituted by up to two unlike members selected from the group consisting of hydroxy, alkoxy having from one to six carbon atoms, carboxy, $C_6H_3R^4R^5$ and $OC_6H_3R^4R^5$ provided that when two of said members are present and are hydroxy and said alkoxy, said members are attached to different carbon atoms; n is 1 to 4, $R^2$ and $R^3$ are each hydrogen or alkyl having from one to four carbon atoms; $R^4$ and $R^5$ are each hydrogen, hydroxy, alkyl or alkoxy having from one to four carbon atoms; further provided that $R^1$ is other than

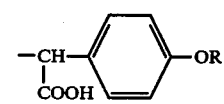

12. A method according to claim 11 wherein said compound is the L-isomer.

13. A method according to claim 12 wherein R is hydrogen.

14. The method according to claim 13 wherein $R^1$ is a member selected from the group consisting of 4-hydroxybenzyl, 2-methoxyethyl, isopropyl, propargyl, cyclopentyl and 2-diethylaminoethyl.

15. A pharmaceutical composition comprising a pharmaceutically acceptable carrier and a blood flow or oxygen availability increasing amount of a compound of claim 1.

16. A method of treating a mammaliam subject suffering from a disease or condition attributable to reduced carbohydrate metabolism which comprises orally or parenterally administering to said subject a carbohydrate metabolism increasing about of an L- or DL-isomer of a compound of the formula

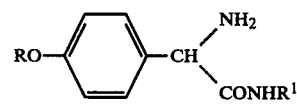

and the pharmaceutically acceptable salts thereof, wherein R is hydrogen or methyl;

$R^1$ is a member selected from the group consisting of alkynyl, alkenyl, cycloalkyl, each having from three to seven carbon atoms, $CH_2COOH$, $(CH_2)_nNR^2R^3$, $CH_2C_6H_3R^4R^5$,

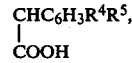

dihydroxyalkyl having from three to four carbon atoms wherein said hydroxy groups are attached to different carbon atoms, and alkyl having from two to six carbon atoms substituted by up to two unlike members selected from the group consisting of hydroxy, alkoxy having from one to six carbon atoms, carboxy, $C_6H_3R^4R^5$ and $OC_6H_3R^4R^5$ provided that when two of said members are present and are hydroxy and said alkoxy, said members are attached to different carbon atoms; n is 1 to 4, $R^2$ and $R^3$ are each hydrogen or alkyl having from one to four carbon atoms; $R^4$ and $R^5$ are each hydrogen, hydroxy, alkyl or alkoxy having from one to four carbon atoms; further provided that $R^1$ is other than

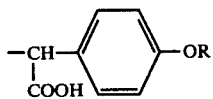

17. A method according to claim 16 wherein said compound is the L-isomer.

18. A method according to claim 17 wherein R is hydrogen.

19. A method according to claim 18 wherein $R_1$ is a member selected from the group consisting of 4-hydroxybenzyl, 2-methoxyethyl, isopropyl. proparagyl, cyclopentyl and 2-diethylaminoethyl.

20. The pharmaceutical composition comprising a pharmaceutically acceptable carrier and a carbohydrate metabolism increasing amount of a compound of claim 1.

* * * * *